(12) United States Patent
Strunk et al.

(10) Patent No.: US 8,984,969 B2
(45) Date of Patent: Mar. 24, 2015

(54) THERMOCHROMIC POLYACRYLAMIDE TISSUE PHANTOM AND ITS USE FOR EVALUATION OF ABLATION THERAPIES

(75) Inventors: Aaron R. Strunk, San Diego, CA (US); Alex Novichenok, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 531 days.

(21) Appl. No.: 13/360,561

(22) Filed: Jan. 27, 2012

(65) Prior Publication Data
US 2013/0192392 A1 Aug. 1, 2013

(51) Int. Cl.
G01N 37/00 (2006.01)
A61B 18/00 (2006.01)
A61B 18/02 (2006.01)
A61B 18/12 (2006.01)
A61B 17/00 (2006.01)
A61N 7/00 (2006.01)

(52) U.S. Cl.
CPC ........... *A61B 18/00* (2013.01); *A61B 18/02* (2013.01); *A61B 18/12* (2013.01); *A61B 2017/00725* (2013.01); *A61B 2018/00809* (2013.01); *A61N 7/00* (2013.01)
USPC .................... 73/865.9; 73/866.4; 600/425

(58) Field of Classification Search
CPC ....................................................... G01N 37/00
USPC ........ 73/1.82, 1.86, 61.46, 432.1, 649, 865.9, 73/866, 866.4; 422/536; 436/272; 116/201, 203, 204; 600/382–385, 372, 600/395, 427, 437–439, 458; 606/32–35
See application file for complete search history.

(56) References Cited

U.S. PATENT DOCUMENTS

| | | | |
|---|---|---|---|
| 6,684,097 B1 * | 1/2004 | Parel et al. .................... | 600/427 |
| 7,294,143 B2 | 11/2007 | Francischelli | |
| 8,118,807 B2 * | 2/2012 | Thiagalingam et al. ........ | 606/32 |
| 2003/0216732 A1 * | 11/2003 | Truckai et al. .................. | 606/49 |
| 2004/0044341 A1 | 3/2004 | Truckai et al. | |
| 2007/0060915 A1 | 3/2007 | Kucklick | |
| 2008/0195089 A1 | 8/2008 | Thiagalingam et al. | |
| 2009/0227999 A1 * | 9/2009 | Willis et al. ..................... | 606/14 |
| 2010/0130836 A1 | 5/2010 | Malchano et al. | |
| 2010/0249774 A1 | 9/2010 | Truckai | |
| 2010/0268112 A1 * | 10/2010 | Short et al. ..................... | 600/549 |
| 2011/0067624 A1 * | 3/2011 | Cain et al. ...................... | 116/201 |
| 2011/0301591 A1 * | 12/2011 | Podhajsky et al. .............. | 606/34 |

FOREIGN PATENT DOCUMENTS

WO 2004071278 A2 8/2004
WO 2008008796 A2 1/2008

OTHER PUBLICATIONS

Lopresto et al., Design and realisation of tissue-equivalent dielectric simulators for dosimetric studies on microwave antennas for interstitial ablation, Oct. 15, 2011,www. ScienceDirect.com, pp. 245-253.*

(Continued)

*Primary Examiner* — Hezron E Williams
*Assistant Examiner* — Hoang Nguyen
(74) *Attorney, Agent, or Firm* — Christopher & Weisberg, P.A.

(57) ABSTRACT

A polyacrylamide tissue phantom embedded with multi-formulated thermochromic liquid crystals for use in the evaluation of RF ablation therapies is provided. The tissue phantom approximates the properties of biological tissue, and therefore provides a suitable substitute for use in testing the effects of RF and other energy-emitting devices on biological tissue. Also provided is a system for using the tissue phantom in the evaluation of RF therapies.

18 Claims, 5 Drawing Sheets

(56) References Cited

OTHER PUBLICATIONS

Gaitini et al., Evaluating Tissue Changes With Ultrasound During Radiofrequency Ablation, Oct. 18, 2007, www.ScienceDirect.com, Ultrasound in Med. & Biol., vol. 34, No. 4, pp. 586-597.*

Butterworth et al., Exploiting Thermochromic Materials for the Rapid Quality Assurance of Physiotherapy Ultrasound Treatment Heads, Sep. 19, 2011, www.ScienceDirect.com, Ultrasound in Med. & Biol., vol. 38, No. 5, pp. 767-776.*

* cited by examiner

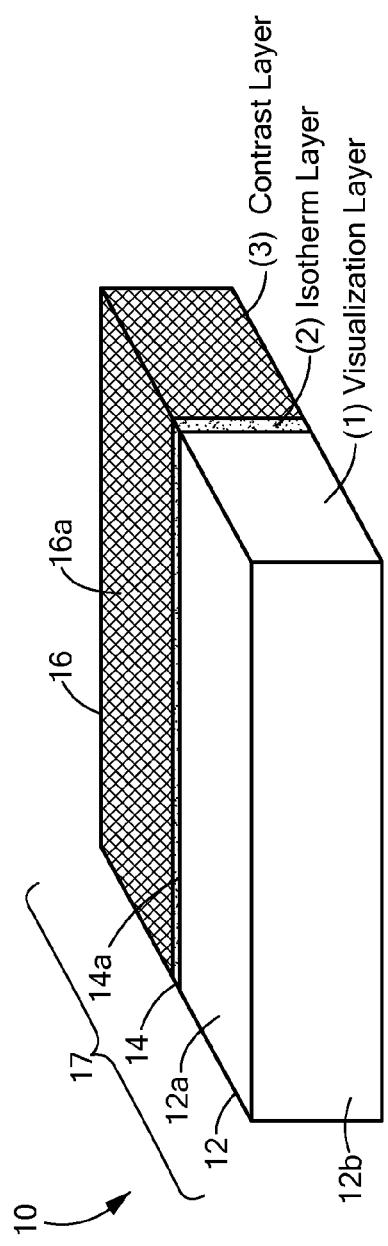
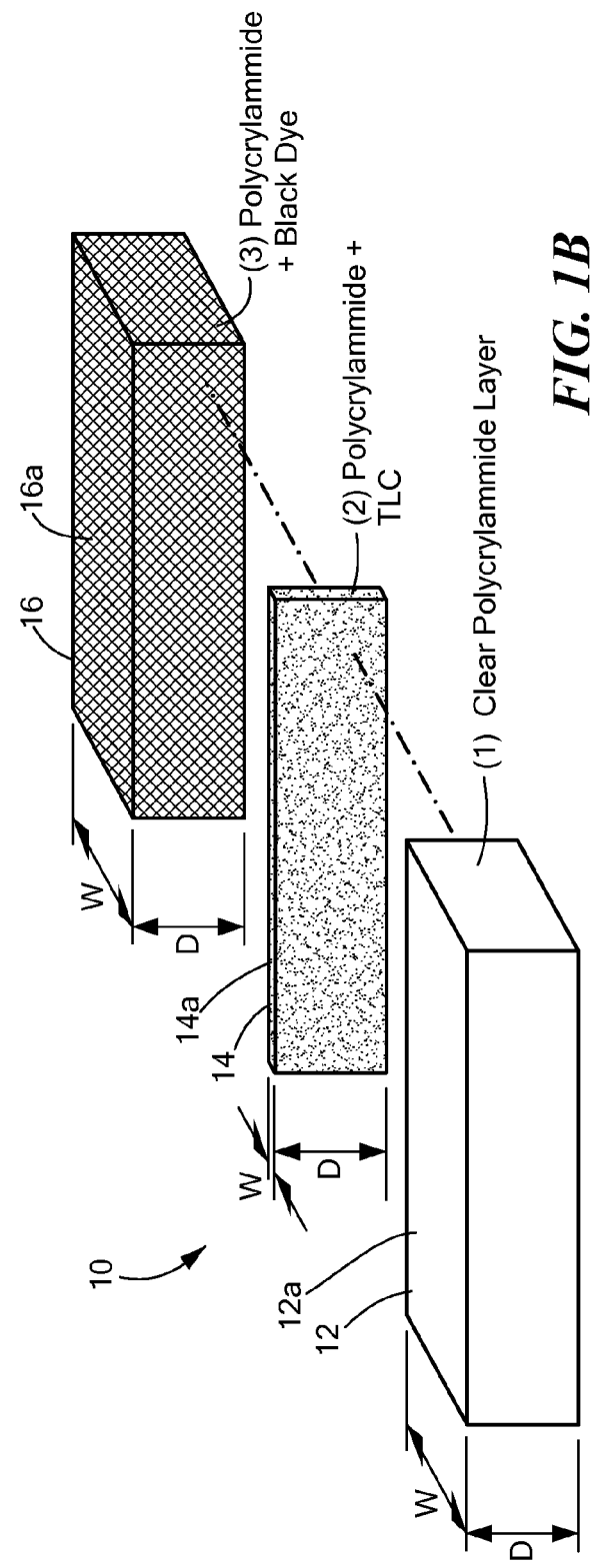
FIG. 1A
FIG. 1B

THERMOCHROMIC POLYACRYLAMIDE TISSUE PHANTOM AND ITS USE FOR EVALUATION OF ABLATION THERAPIES

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for evaluating radiofrequency ablation techniques.

BACKGROUND OF THE INVENTION

Ablation therapy, such as radio frequency ablation (RFA), is commonly used medical procedure in which body tissue is ablated, shrunk, heated, coagulated, or otherwise treated using energy (for example, radio frequency energy). Common examples of ablation therapies include the treatment of cardiac arrhythmia, tumor destruction, pain amelioration, and controlling bleeding. Radio frequency ablation devices, for example, may include a power source and/or RF generator, and one or more ablation elements or electrode coupled to the power source.

The efficacy of RFA and other ablation therapies may depend on such parameters as the type of tissue being treated, the tissue depth to which the RF energy reaches, and the type and spacing of electrodes used. Also, because ablation typically affects tissue at a depth beneath the tissue surface, it can be difficult to accurately analyze the outcome of ablation treatments, including visualization of the ablation pattern and ablation tissue depth. Further, using tissues such as non-living porcine or cadaver tissues can produce a wide variation in results because of the non-uniformity of the samples and the subjective interpretation of results. The effectiveness of ablation therapies using these methods may only be assessed after cutting, staining, and subjectively observing the test tissue. All of these factors can make testing new ablation devices and methods costly and inaccurate. Tissue phantoms provide uniform characteristics and are sometimes used as substitutes for biological tissue, the properties of which can differ substantially from sample to sample. For example, heart phantoms may be used for analysis of cardiac motion and freezing properties of cardiac tissue; lung phantoms may be used for calibration of medical CT scanners; and entire phantom torsos, including organs, maybe used for laparoscopic technique training. However, just like biological tissue, it is not always easy to visualize the effects on these tissue phantoms of the medical or testing procedure. Also, many commonly used tissue phantom materials, such as agar, may have a melting point that is lower than the testing temperature.

During ablation, in particular RFA, it is important to monitor the temperature of the electrode to prevent ablation of unintended tissue areas and depths, and to prevent the electrode from overheating. Because thermochromic materials may provide visualization of minute temperature gradients, as well as binary threshold temperature confirmation, they are especially useful in the medical industry. Thermochromic materials and compounds may be used to indicate when an electrode reaches a certain threshold temperature. For example, binary thermochromic materials may be colored and opaque at room temperature, but become transparent when the threshold temperature is reached. Common uses for thermochromic materials include thermochromic thermometers, battery charge indicators, and color-change dyes. However, the use of thermochromic materials has not yet been adapted for use in the evaluation of such medical procedures as RFA.

To accurately evaluate the effectiveness of RFA and other ablation therapies, it is desired to provide a tissue phantom that could mimic a variety of mammalian tissues and that gives visual confirmation of the temperature gradient produced within the tissue phantom by the application of RF energy. Such a device and method of use would reduce variability in test setup and decrease overall testing time, allowing for a statistically significant number of tests to be conducted in less time than traditional testing methods.

SUMMARY OF THE INVENTION

The present invention advantageously provides a device and method for reliably and consistently measuring the thermal effects of ablation therapies. In one embodiment, the device may comprise a substance mimicking mammalian body tissue and changing color in response to contact with an activated ablation device. The substance may be a layered substance, at least one layer being a thermochromic layer. The layered substance may further include a substantially transparent second layer having a first surface, and a substantially opaque third layer having a first surface, the thermochromic layer being between the second and third layers. Further, the layered substance may be composed at least in part of polyacrylamide gel, which may be doped with other compounds, such as salts. The thermochromic layer changes color in response to energy such as radiofrequency energy, radiant heat, cooling, microwave energy, or electromagnetic energy. The thermochromic layer may include microencapsulated cholesteric liquid crystals, and may include a plurality of formulations of liquid crystals. Further, each of the plurality of formulations may have a bandwidth of between approximately 1° C. and approximately 20° C., and the thermochromic layer may respond to radiofrequency energy over a temperature range of approximately 50° C. to approximately 110° C.

In another embodiment, the device may comprise: a layered polyacrylamide gel mimicking body tissue, including a substantially transparent first layer having a first surface and a second surface; a thermochromic second layer having a first surface and including thermochromic microencapsulated cholesteric crystals that change color in response to ablation energy over a temperature range of approximately 50° C. to approximately 110° C., a substantially opaque third layer having a first surface and providing contrast to the second layer, the second layer being between the first and third layers; and an energy application surface comprising the first surface of each of the first, second, and third layers, the width of the thermochromic second layer being between approximately 0.5 mm to approximately 1.5 mm as measured on the energy application surface, the width being substantially constant throughout the thermochromic second layer. Further, the second and third layers may each have a width of between approximately 15 mm and approximately 20 mm as measured on each of the first surfaces of the second and third layers.

The method may comprise providing a substance mimicking mammalian tissue, the substance having a substantially transparent first layer having a first surface and a second surface; a thermochromic second layer having a first surface and including thermochromic material that changes color in response to contact with an activated ablation device, a substantially opaque third layer having a first surface and being suitable for providing contrast to the second layer, the second layer being between the first and third layers, providing an ablation device; activating the ablation device and placing the device in contact with at least the first surface of the thermochromic second layer, observing through the second surface of the substantially transparent first layer the color changes in the second thermochromic layer, determining whether to adjust parameters of the ablation device based on the color changes. The method may further include providing a tank containing a volume of electrically conductive fluid, providing a fluid flow chamber in fluid communication with the tank and including a pump for circulating the fluid between the tank and the flow chamber, placing the substance within the tank so that at least the first surface of the thermochromic second layer is submerged within the fluid, providing a camera having a telecentric lens and being positioned in visual communication with the second surface of the substantially transparent first layer, placing an activated ablation device in contact with at least the first surface of the thermochromic second layer, and visualizing color changes in the thermochromic second layer through the second surface of the substantially transparent first layer using the lens of the camera. The thermochromic material includes cholesteric liquid crystals, which may be microencapsulated. The thermochromic material changes color in response to at least one of radiofrequency energy, radiant heat, cooling, microwave energy, and electromagnetic energy. Further, the thermochromic material may respond to radiofrequency energy over a temperature range of approximately 40° C. to approximately 120° C. Further, the thermochromic material may include a plurality of formulations of liquid crystals, each of formulations having a bandwidth of approximately 20° C. or less.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1A shows a perspective view of an example of a material that mimics mammalian tissue;

FIG. 1B shows an exploded view of an example of a material that mimics mammalian tissue;

DETAILED DESCRIPTION OF THE INVENTION

Figure 2:
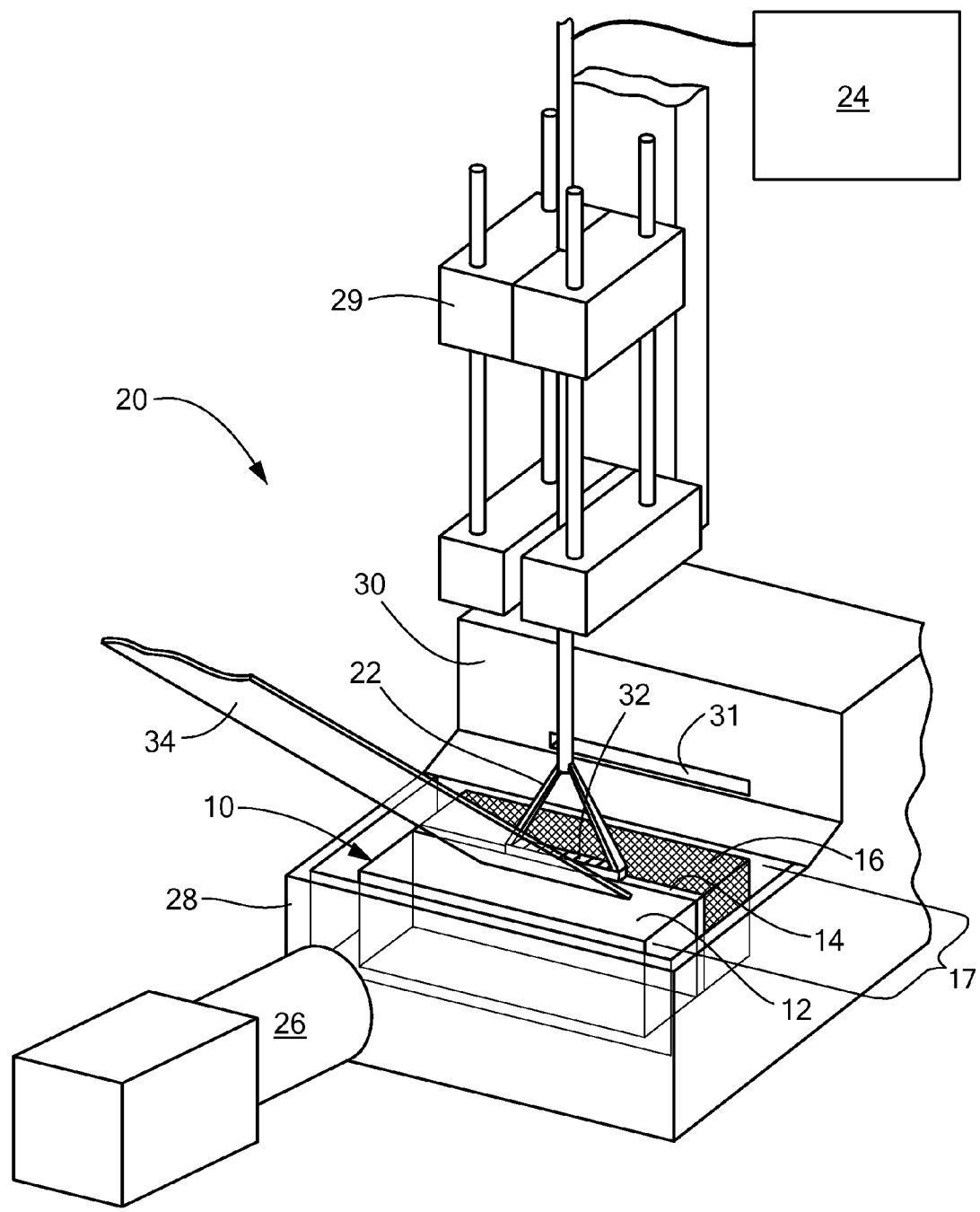
FIG. 2 shows a schematic view of a testing system.

The present invention advantageously provides a method and system for reliably and consistently measuring the thermal effects of ablation therapies, and may be used to evaluate effectiveness of various ablation devices.

As used herein, reference to the tissue phantom "mimicking mammalian tissue" means that the tissue phantom has one or more properties that are substantially consistent with living mammalian tissue. Such properties may include thermal conductivity, electrical conductivity, pH, texture, water content, and others.

As used herein, any reference to ablation, ablation technology, or ablation device, may include any type of same, unless otherwise specified. Such ablation technologies may include radiofrequency ablation, cryoablation, ultrasound ablation, laser ablation, or others. An ablation device as used herein may be any device that is capable of emitting energy (such as an RFA catheter) or absorbing energy (such as a cryoablation catheter). Likewise, an "energy generator" as used herein may be a device that creates energy (such as an RF generator) or provides for the removal of energy (such as a Peltier cooler or thermoelectric cooler). Accordingly, reference to "applying energy" herein may also be interpreted to include the removal of energy.

Referring now to FIGS. 1A and 1B, a perspective view and an exploded view of an example of a material that mimics mammalian tissue are shown. The material may be a layered thermochromic tissue phantom 10 that changes color when in contact with an activated ablation device. The layered thermochromic tissue phantom 10, generally referred to herein as "tissue phantom," may be composed of polyacrylamide or other substance having substantially similar characteristics, although the tissue phantom 10 may also include other ingredients. The tissue phantom 10 may be in a substantially gel state (that is, the tissue phantom 10 is solid enough to hold a desired shape). Polyacrylamide gel (PAG) is well suited for use in evaluating ablation therapies and devices because the PAG may be doped with a salt to mimic the electrical conductivity of various human tissues, for example, NaCL or KCl. Additionally, PAG has a melting point that is higher than the temperature range optimal for testing ablation therapies, both at the surface and below the surface of the PAG (subsurface temperatures may be higher than the surface temperature). The tissue phantom 10 may include a plurality of polyacrylamide layers, depending on the one or more compounds added to a particular layer. For example, as shown in FIG. 1, the tissue phantom 10 includes three layers. The first layer 12 may be composed essentially of substantially transparent polyacrylamide, the second layer 14 may be composed essentially of polyacrylamide embedded with a thermochromic material that changes color in response to the application of energy (such as RF energy), and the third layer 16 may be substantially opaque and composed essentially of polyacrylamide and dye. Each layer 12, 14, 16 has a first surface 12a, 14a, 16a, respectively, the first surfaces 12a, 14a, 16a together comprising an energy application surface 17 (however, this could also be the surface from which energy is removed, such as when testing cryoablation devices). Widths and depths of the layers 12, 14, 16 are determined as depicted by the bracketed areas in FIG. 1B.

In order to test an ablation device, the electrodes of the device are placed on the energy application surface 17. The electrodes are placed in contact with at least the first surface 14a of the second layer 14, but may also be placed in contact with the first surfaces 12a, 16a of the first 12 and third 16 layers. The thermal effects of the activated ablation device may be observed in the second layer 14. Color changes in the thermochromic second layer 14 are not permanent, and so the tissue phantom 10 may be used for multiple tests.

Continuing to refer to FIGS. 1A and 1B, the first layer 12 of clear polyacrylamide is referred to as the "visualization layer" because it may be possible to see the thermochromic second layer 14 through this first layer 12. In one non-limiting embodiment, the first surface 12a of the visualization layer 12 is between approximately 15 mm and approximately 20 mm wide, as measured at the first surface 12a. However, the visualization layer 12 may have any width that permits undistorted viewing therethrough of the second layer 14. The visualization layer 12 may also have a second surface 12b through which the thermochromic second layer 14 may be visible.

Continuing to refer to FIGS. 1A and 1B, the second layer 14 of polyacrylamide embedded with thermochromic material is referred to as the "TLC" layer. In one non-limiting embodiment, the TLC layer 14 is between approximately 0.5 mm and approximately 1.5 mm as measured on the first surface 14a, the width being substantially constant throughout the layer. For example, the layer may have a standard deviation of ±0.5 mm. Within this width range, the TLC layer 14 may be thick enough to hold an amount of thermochromic liquid crystals sufficient for testing purposes, but also be thin enough to precisely visualize color changes.

The thermochromic material may be water-miscible, microencapsulated thermochromic liquid crystals (referred to herein as "TLC compound"), such as cholesteric crystals (for example, cyanobiphenyls and cholesteryl nonanoate), chiral nematic crystals, or combination thereof. Although the mechanism by which all of these thermochromic liquid crystals change color may be the same, cholestric and chiral nematic formulations may have different chemical and physical characteristics. For simplicity, however, all are collectively referred to with the generally accepted nomenclature of "cholesteric liquid crystals." The TLC compound includes one or more thermochromic formulations, the number and characteristics of the formulations depending on the desired temperature range to be represented in color gradients. As shown and described in FIG. 4, these gradients substantially correspond to the dimension of a lesion created in biological tissue. Based on these visual effects, a user may adjust such features of the ablation device as number, size, distribution, and type of electrodes used.

Continuing to refer to FIGS. 1A and 1B, the third layer 16 of polyacrylamide and dye is referred to as the "contrast layer." The dye may be a dark-colored dye, such as a black dye (for example, Brilliant Black dye), in order to enhance the colors of the TLC layer 14 when viewed through the visualization layer (that is, provide contrast to the TLC layer 14). The dye should be water-miscible, and should not be added in a concentration that would result in leeching into or otherwise affecting or distorting the TLC layer 14. In one non-limiting embodiment, the contrast layer 16 is between approximately 15 mm and approximately 20 mm wide, as measured at the first surface 16a. However, the contrast layer 16 may have any width that provides an adequate background for visualization of the TLC layer 14.

An ablation device is applied to the tissue phantom 10, with the one or more electrodes at least in contact with the first surface 14a of the TLC layer 14, although the electrodes may also be in contact with the first surfaces 12a, 16a of the visualization layer 12 and contrast layer 16 as well. When placed in contact with the tissue phantom 10, the activated ablation device may have no perceivable effect on the visualization and contrast layers 12, 16; however, contact with the activated ablation device will produce colored gradients within the TLC layer 14 that correspond to the temperature of the TLC layer within the temperature range of the TLC compound. For example, as shown and described in FIG. 3, the TLC compound may be formulated to respond to radiofrequency energy over a temperature range of approximately −30° C. to approximately 120° C., although a temperature range of approximately 40° C. to approximately 120° C. may be used when testing such ablation therapies such as RF ablation.

In a non-limiting example, four different thermochromic crystal formulations may be combined in the TLC compound. A first formulation may have a red start (the temperature at which a clear PAG will turn a red color) at approximately 50° C. and a bandwidth of approximately 2° C. This means that this formulation may cause thermally affected areas of the TLC layer 14 to turn red at approximately 50° C., to turn mid-green at approximately 51° C., and to turn blue at approximately 52° C. (an overall 2° C. bandwidth). The blue color will persist until a clearing temperature is reached and the PAG turns clear. At this clearing point, a second formulation may begin showing color. For example, a second formulation may have a red start at approximately 60° C. and a bandwidth of approximately 2° C., a third formulation may have a red start at approximately 70° C. and a bandwidth of approximately 2° C., and a fourth formulation may have a red start at approximately 80° C. and a bandwidth of approximately 2° C. The thermochromic crystals in each formulation may appear colorless below and above the appropriate bandwidth temperatures, only displaying color when the temperature is within the bandwidth for the formulation. Thus, in this example, the TLC layer 14 displays color representation over a temperature range of approximately 50° C. to approximately 82° C. (through the anisotropic chiral or twisted nematic phase), and appears colorless below approximately 50° C. (crystallic phase) and above approximately 82° C. (isotropic phase/clearing point). This temperature range is appropriate for evaluating most ablation therapies and devices because a chronic lesion (that is, tissue ablation) may occur at approximately 50° C. and above, such as when using RF ablation. Further, using formulations with a small bandwidth (for example, 2° C. as compared to a bandwidth of 20° C.) makes the color bands narrower, so a single band can be isolated from which to draw data points instead of judging temperature based on hue in wider color bands resulting from a formulation having a larger bandwidth. However, formulations may be provided that display color representation over a temperature range of approximately −30° C. to approximately 120° C.

It should be noted that the overall polyacrylamide formulation used in all layers of the tissue phantom 10 may be adjusted to mimic a variety of test tissues. For example, the PAG may be doped with various amounts a salt such as NaCl to mimic the electrical conductivity of different mammalian tissues. Additionally, the PAG may be doped with other compounds to adjust such parameters as the thermal conductivity, pH, and moisture content of the tissue phantom 10. For example, glycerol may be added to the PAG to adjust thermal properties of the tissue phantom 10. The tissue phantom 10 may also be molded to resemble any shape, including human internal organs. No matter what the shape of the tissue phantom 10, however, the tissue phantom 10 may still include a visualization layer 12, a TLC layer 14, and a contrast layer 16. Further, the TLC layer may be between 0.5 mm and 1.5 mm wide, as measured at the first surface 14a, the width being substantially constant throughout the layer. Further, a substantially flat (planar) TLC layer 14 may enhance viewability of the color representation within. Further, for irregular tissue phantom 10 shapes, the visualization 12 and contrast 16 layers may each have a depth that is greater or less than the TLC layer 14; however, the depths of the visualization 12 and contrast 16 layers may be at least equal to the active area of the TLC layer 14 (that is, the area over which color representation is displayed).

Referring now to FIG. 2, a schematic view of a testing system 20 is shown. In one embodiment, the testing system includes a tissue phantom 10, an ablation device 22 and energy generator 24 (such as an RF generator) for the application of energy to the tissue phantom 10, a camera 26 for imaging color gradients in the tissue phantom 10, a tank 28 for containing saline or other electrically conductive fluid, a device holder 29 for holding the ablation device 22 in position, a flow chamber 30 for generating and adjusting the flow of electrically conductive fluid through the tank 28, and a flow nozzle 31 in fluid communication with the flow chamber 30 and tank 28.

Continuing to refer to FIG. 2, the ablation device 22 (such as an RF ablation device) and energy source 24 (such as an RF generator) may be used to apply (or remove) energy to the tissue phantom 10. Accordingly, the TLC layer 14 compound may be adjusted as necessary to produce color representation in the relevant temperature range. The ablation device 22 may be stabilized and held within a device holder 29 positioned above the tissue phantom 10, which may be either integrated with a part of the system (for example, affixed to the tank 28) or be a free-standing frame or device. In one embodiment, a multi-array ablation catheter (for example, Ablation Frontiers MAAC® Multi-Array Ablation Catheter®) and RF generator (for example, Ablation Frontiers GENius™ Multi-Channel RF Generator) are used. The device 22 may include one or more electrodes 32, which may be composed of platinum or other electrically conductive metal. The generator 24 may include one or more energy modes (for example, bipolar, unipolar, 4:1, 2:1, and 1:1 modes of an RF generator). During testing, parameters such as electrode 32 number and spacing and generator 24 modes may be adjusted and resulting effects on the TLC layer 14 of the tissue phantom 10 evaluated.

Continuing to refer to FIG. 2, a camera 26 may be used to image color gradients within the TLC layer 14 of the tissue phantom 10. The camera 26 may be affixed to the tank 28 or otherwise positioned for an unimpeded view of the tissue phantom 10 within the tank 28 (in visual communication with the second surface 12b of the visualization layer 12). The camera 26 may be, for example, a CCD or CMOS camera, may have an internal or external power source, and may be in electrical communication with a computer or other data storage device. Additionally, the camera 26 may be capable of producing still images, video images, or both. Alternatively, a lens (simple lens or compound lens) or the naked eye may be used to image the color representation in the tissue phantom 10. In one embodiment, a video camera having a telecentric lens is used, as shown in FIG. 2. A video of the tissue phantom 10 as energy is applied may be taken by the camera 26, in order to evaluate the change in temperature of the tissue phantom 10 over time. Or, the camera 26 may take a series of still images (for example, at the rate of one frame per second), which can be used to evaluate color representation over time.

Continuing to refer to FIG. 2, a tank 28 and flow chamber 30 may be used to contain and control the flow of an electrically conductive fluid, such as saline. The tissue phantom 10 may be placed within the tank 28 so that at least the first surface 14a of the TLC layer 14 may be in contact with the electrically conductive fluid. The flow chamber 30 may be in fluid communication with the tank 28 and may include a pump in connection with a power source for circulating the fluid within the tank 28 and between the tank 28 and the flow chamber 30. For example, the electrically conductive fluid may flow from the flow chamber 30 to the tank 28 through a flow nozzle 31 that applies an adjustable stream of fluid over the ablation surface 17 of the tissue phantom 10. The electrically conductive fluid, and flow thereof, may be a variable that is adjusted for evaluating the effects of energy emission (such as RF energy emission) on the tissue phantom 10. Additionally, the flow rate of the fluid may affect the power and temperature of the device 22 being tested. This effect may be useful when testing device 22 technology, for example, when testing the efficiencies of various RFA electrodes. Alternatively, however, an electrically conductive fluid may not be used, and instead the results of the therapy on the tissue phantom 10 may be evaluated without accounting for the effects of the fluid.

Continuing to refer to FIG. 2, the system 20 may further include one or more glare shields 34 for reducing glare from the electrodes that may hinder visualization of the color representation in the TLC layer 14. Further, the system 20 may include a dark contrast backdrop (against which the entire tissue phantom 10 may be viewed), one or more light sources, frames, clamps, hoses, conduits, connectors, valves, power sources, displays, computers, user input devices, user control devices, and other components for efficient device 22 testing and system 20 operation. Further, the system 20 may be operable by or in cooperation with automated capture and analysis software.

Figure 3:
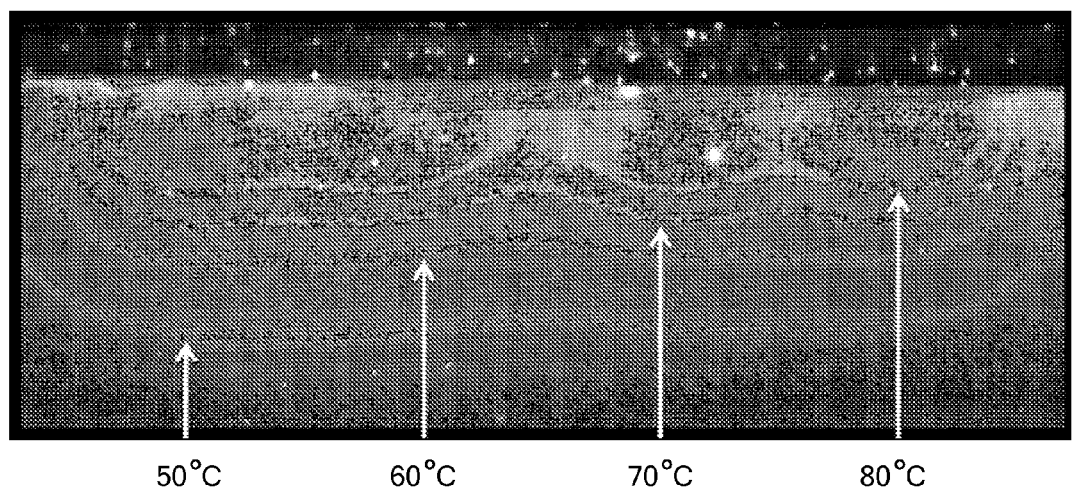
FIG. 3 shows a close-up cross-sectional image of a thermally affected layered thermochromic tissue phantom sample.

Referring now to FIG. 3, a close-up cross-sectional image of a thermally affected layered thermochromic tissue phantom sample is shown. As shown and described in FIG. 1, the TLC compound displays colors corresponding to a range of temperatures (color representation), for example, from approximately 50° C. to approximately 100° C. As a non-limiting example, an RFA device 22 such as an Ablation Frontiers MAAC® Multi-Array Ablation Catheter® may be used with an Ablation Frontiers GENius™ Multi-Channel RF Generator 24. As shown and described in FIG. 4, the color representation of FIG. 3 substantially corresponds to the dimensions of an RFA lesion created in biological (mammalian) tissue. A computer program or mathematical formula may be used to interpolate temperature between bands of the color representation and to extrapolate temperature beyond the temperature range within each color band based on the one or more TLC formulations used in the TLC layer 14. Areas of the TLC layer 14 that are at a temperature above or below the temperature range of the one or more combined TLC formulations appear transparent or uncolored.

Figure 4:
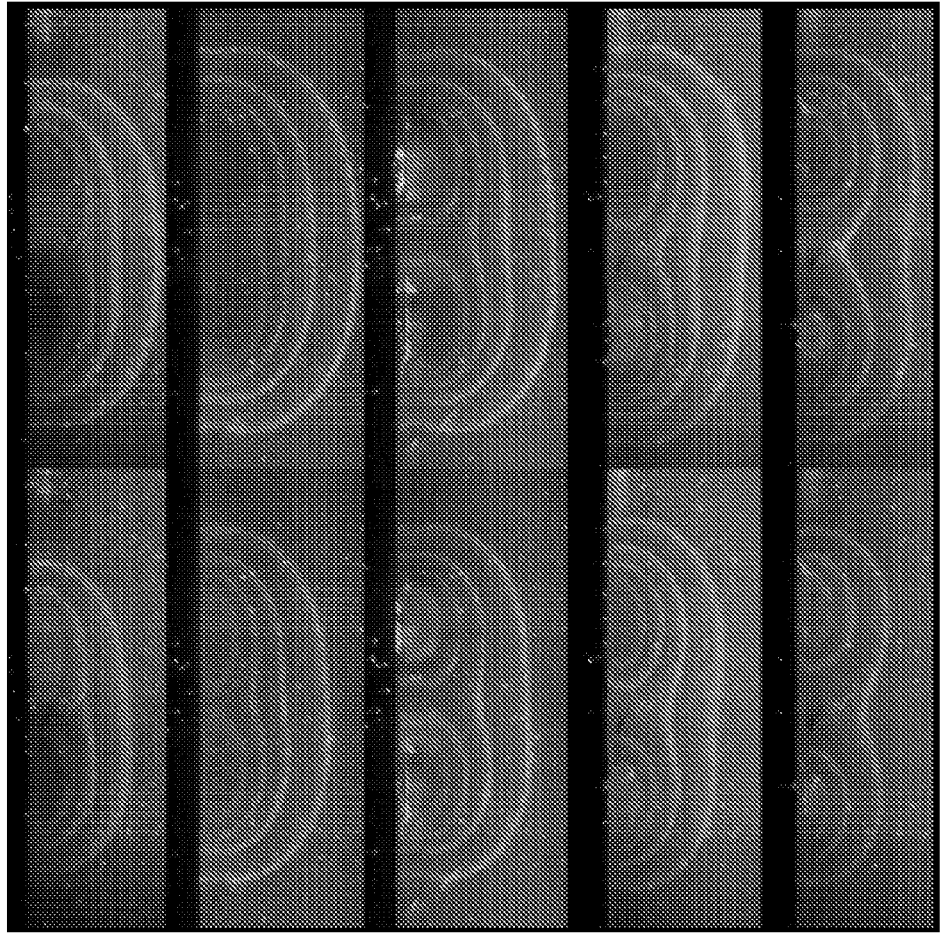
FIG. 4 shows cross-sectional images of the layered thermochromic tissue phantom sample, as when evaluating the effects of electrode spacing on lesion development.

Referring now to FIG. 4, cross-sectional images of the layered thermochromic tissue phantom sample 10, as when evaluating the effects of electrode 32 spacing on lesion development, are shown. FIG. 4 is a non-limiting example of the type of ablation device data that can be gathered using a tissue phantom 10. The term "set point" refers to the temperature to which at least a portion of the device 22 is brought. For example, a 55° C. set point means that the electrodes 32 of an ablation device 22 are brought to and maintained at a temperature of 55° C. Then, the thermal effects on the tissue phantom 10 at this electrode temperature setting may be evaluated by visualizing color representation in the TLC layer 14. Because the color representation corresponds to a lesion created in mammalian tissue, a user can easily and accurately evaluate subsurface effects of a device 22 when operated at various set points. Based on these visual effects, a user may adjust the device 22 by, for example, adjusting the spacing between electrodes 32.

Figure 5:
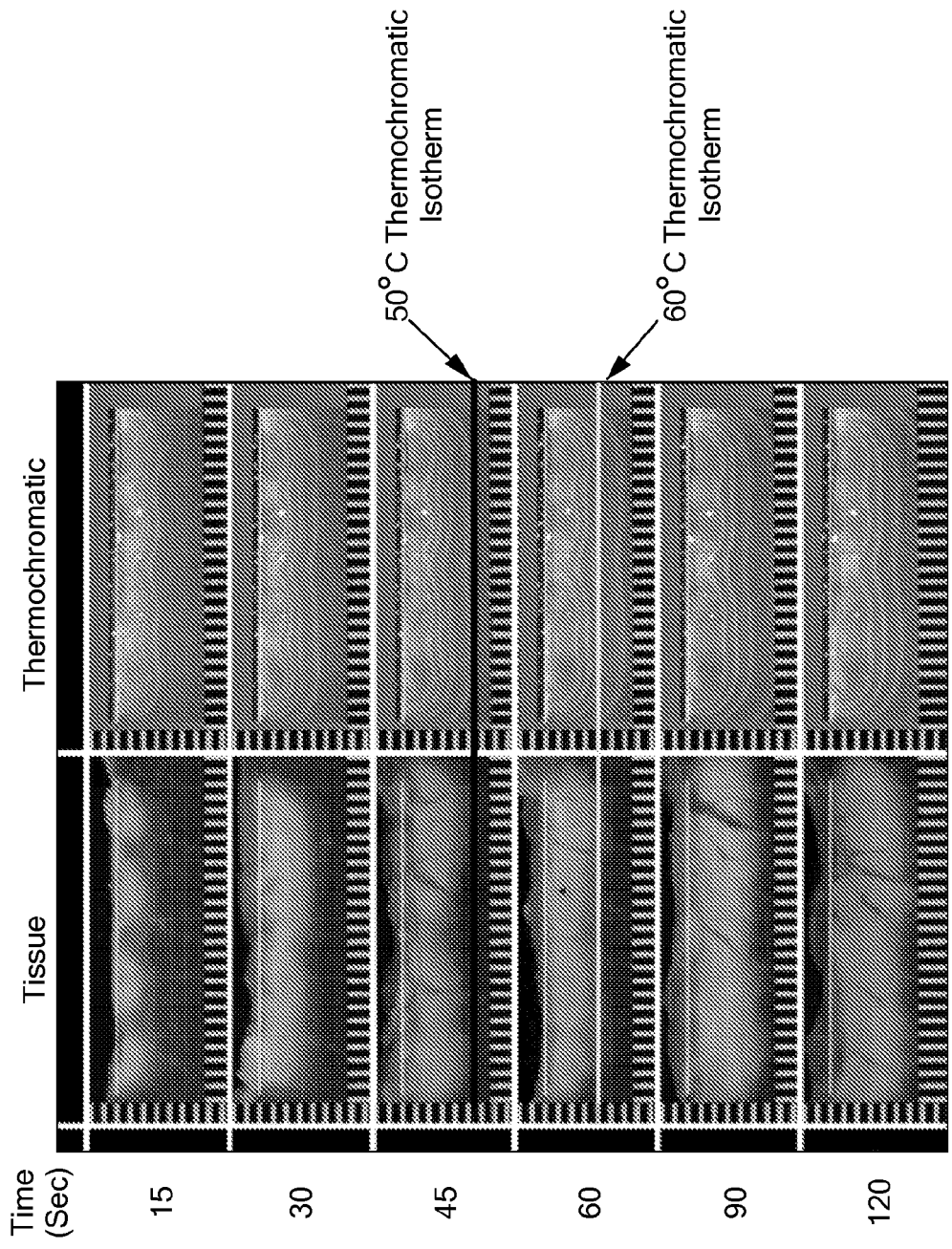
FIG. 5 shows a chart of cross-sectional images of both porcine tissue and layered thermochromic tissue phantom to compare lesion development in both tissues over time.

Referring now to FIG. 5, a chart of cross-sectional images of both porcine tissue and layered thermochromic tissue phantom to compare lesion development in both tissues over time are shown. This series of images illustrates the suitability of the tissue phantom 10 as a replacement for mammalian tissue during testing. That is, the series of images shows that the areas of TLC layer 14 in the tissue phantom 10 very closely correspond to the lesions created in biological tissue using the same energy application method. In the first (left-hand) column of the chart, the time course over which energy is applied is shown. For this series of images, an RF generator set to 4:1 energy mode is used. In the second and third columns, the thermal affects of energy application on both mammalian tissue (for example, porcine thigh muscle tissue) and the tissue phantom 10 is shown, respectively. For example, RF energy may be applied to both mammalian tissue and the tissue phantom 10 over a course of two minutes, with the effects on both tissues being compared at 15-second or 30-second intervals. The 45- and 60-second interval images each include a faint transition zone corresponding to an isotherm line: a 50° C. isotherm line is shown in the 45-second interval images of mammalian tissue and tissue phantom, and a 60° C. isotherm line is shown in the 60-second interval images of mammalian tissue and tissue phantom. These lines demonstrate the correlation between color representation of temperature in the TLC layer 14 of the tissue phantom 10 and the lesion created in mammalian tissue. In FIG. 4, an RFA device and RF generator set to 4:1 mode are used for the treatment of both tissues. For each time interval in FIG. 4, the mammalian tissue was first cut and stained with 2,3,5-Triphenyltetrazolium chloride (TTC) before an image was taken of the lesion. In contrast, the color representation in the TLC layer 14 of the tissue phantom 10 was easily imaged in real-time without the need for cutting, staining, or otherwise altering the tissue phantom 10.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A device for testing ablation devices comprising:
   a layered substance mimicking mammalian tissue and changing color in response to contact with an activated ablation device, the substance including:
   a thermochromic first layer having a first surface;
   a substantially transparent second layer having a first surface;
   a substantially opaque third layer having a first surface, the thermochromic first layer being between the second and third layers; and
   an energy application surface comprising the first surface of the thermochromic first layer, the first surface of the substantially transparent second layer, and the first surface of the substantially opaque third layer.

2. The device of claim 1, wherein the layered substance is composed at least in part of polyacrylamide gel.

3. The device of claim 2, wherein the polyacrylamide gel is doped with a compound from the group consisting of: salts and glycerol.

4. The device of claim 1, wherein the thermochromic first layer is between approximately 0.5 mm and approximately 1.5 mm wide as measured on the first surface of the thermochromic first layer, the width being substantially constant throughout the thermochromic first layer.

5. The device of claim 1, wherein the thermochromic first layer changes color in response to at least one of the group consisting of: radiofrequency energy, radiant heat, cooling, microwave energy, and electromagnetic energy.

6. The device of claim 1, wherein the thermochromic first layer includes microencapsulated cholesteric liquid crystals.

7. The device of claim 6, wherein the thermochromic first layer includes a plurality of formulations of liquid crystals.

8. The device of claim 7, wherein the each of the plurality of formulations has a bandwidth of between approximately 1° C. and approximately 20° C.

9. The device of claim 1, wherein the thermochromic first layer responds to radiofrequency energy over a temperature range of approximately 50° C. to approximately 110° C.

10. A device for testing radiofrequency ablation therapies comprising:
    a layered polyacrylamide gel mimicking body tissue, including
    a substantially transparent first layer having a first surface and a second surface;
    a thermochromic second layer having a first surface and including thermochromic microencapsulated cholesteric crystals that change color in response to radiofrequency energy over a temperature range of approximately 50° C. to approximately 110° C.;
    a substantially opaque third layer having a first surface and providing contrast to the second layer, the second layer being between the first and third layers; and
    an energy application surface comprising the first surface of each of the first, second, and third layers, the width of the thermochromic second layer being between approximately 0.5 mm to approximately 1.5 mm as measured on the energy application surface, the width being substantially constant throughout the thermochromic second layer.

11. The device of claim 10, wherein the second and third layers each have a width of between approximately 15 mm and approximately 20 mm as measured on each of the first surfaces of the second and third layers.

12. A method of testing radiofrequency ablation devices comprising:
    providing a substance mimicking mammalian tissue, the substance having:
    a substantially transparent first layer having a first surface and a second surface;
    a thermochromic second layer having a first surface and including thermochromic material that changes color in response to contact with an activated ablation device;
    a substantially opaque third layer having a first surface and being suitable for providing contrast to the second layer, the second layer being between the first and third layers,
    the first surface of the substantially transparent first layer, the first surface of the thermochromic second layer, and the first surface of the substantially opaque third layer together comprising an energy application surface;
    providing an ablation device;
    activating the ablation device and placing the device in contact with energy application surface;
    observing through the second surface of the substantially transparent first layer the color changes in the second thermochromic layer; and
    determining whether to adjust parameters of the ablation device based on the color changes.

13. The method of claim 12, furthering including:
    providing a tank containing a volume of electrically conductive fluid;
    providing a fluid flow chamber in fluid communication with the tank and including a pump for circulating the fluid between the tank and the flow chamber;
    placing the substance within the tank so that at least the first surface of the thermochromic second layer is submerged within the fluid;

providing a camera having a telecentric lens and being positioned in visual communication with the second surface of the substantially transparent first layer;

placing an activated ablation device in contact with at least the first surface of the thermochromic second layer; and visualizing color changes in the thermochromic second layer through the second surface of the substantially transparent first layer using the lens of the camera.

14. The method of claim 12, wherein the thermochromic material includes microencapsulated cholesteric liquid crystals.

15. The method of claim 14, wherein the thermochromic material changes color in response to at least one of the group consisting of: radiofrequency energy, radiant heat, cooling, microwave energy, and electromagnetic energy.

16. The method of claim 12, wherein the thermochromic second layer is between approximately 0.5 mm and approximately 1.5 mm wide as measured on the first surface, the width being substantially constant throughout the layer.

17. The method of claim 15, wherein the thermochromic material responds to radiofrequency energy over a temperature range of approximately 40° C. to approximately 120° C.

18. The method of claim 15, wherein the thermochromic material includes a plurality of formulations of liquid crystals, each of formulations having a bandwidth of approximately 20° C. or less.

\* \* \* \* \*